United States Patent [19]
Larson et al.

[11] Patent Number: 5,624,572
[45] Date of Patent: Apr. 29, 1997

[54] POWER MANAGEMENT SYSTEM AND METHOD FOR MAXIMIZING HEAT DELIVERED TO DIALYSATE IN A DIALYSIS MACHINE

[75] Inventors: Byron Larson, Arvada; Frank Ogawa, Lakewood, both of Colo.

[73] Assignee: Cobe Laboratories, Inc., Lakewood, Colo.

[21] Appl. No.: 485,114

[22] Filed: Jun. 7, 1995

[51] Int. Cl.$^6$ .................................................. B01D 61/32
[52] U.S. Cl. .......................... 210/746; 210/149; 210/646; 210/742; 219/497; 307/39; 340/640; 604/5
[58] Field of Search .................................. 210/149, 175, 210/184, 646, 742, 774, 929, 138, 739, 746; 219/490, 492, 497; 340/640, 655, 664; 604/4, 5, 6; 364/413.01, 413.02, 413.07; 165/1, 11.1, 13, DIG. 2; 307/39

[56] References Cited

U.S. PATENT DOCUMENTS

| | | | |
|---|---|---|---|
| 4,167,663 | 9/1979 | Granzow et al. | 219/497 |
| 4,370,983 | 2/1983 | Lichtenstein | 210/929 |
| 4,389,640 | 6/1983 | Dawdy | 340/640 |
| 4,628,186 | 12/1986 | Bergemann et al. | 219/497 |
| 5,326,476 | 7/1994 | Grogan et al. | 210/929 |
| 5,472,614 | 12/1995 | Rosse | 604/4 |
| 5,487,827 | 1/1996 | Peterson et al. | 604/4 |

*Primary Examiner*—Joseph W. Drodge
*Attorney, Agent, or Firm*—John R. Ley

[57] ABSTRACT

The amount of electrical power delivered to a dialysate heater in the dialysis machine is maximized without substantially exceeding a predetermined maximum allowed power consumption for the dialysis machine. The instantaneous power consumed by the machine is measured and compared to the maximum allowed power consumption. The excess of power beyond the instantaneous power consumed up to the maximum allowed power consumption is then made available to the heater. The worst case power consumption limitations of the dialysis machine components do not adversely affect the heat available from the heater. The rate at which dialysis treatments may progress may increase or the time required for dialysis treatments may decrease.

16 Claims, 4 Drawing Sheets

POWER MANAGEMENT SYSTEM AND METHOD FOR MAXIMIZING HEAT DELIVERED TO DIALYSATE IN A DIALYSIS MACHINE

This invention relates generally to dialysis machines and more particularly, to a new and improved power management system and method for maximizing the amount of electrical power delivered to a heater for a flow of dialysate supplied during a dialysis treatment.

BACKGROUND OF THE INVENTION

In general, a dialysis machine is used as a substitute for the natural kidney functions of a human body. As such, the dialysis machine cleans the blood of the natural accumulation of bodily wastes and separates the wastes from the blood outside the body or extracorporeally. The separated wastes are discharged and the cleansed blood is returned to the body.

A dialysis machine uses a dialyzer to separate the wastes from the blood. The dialyzer includes a porous medium located within a closed housing which separates the housing into a blood compartment and a dialysate compartment. The blood removed from the patient flows through the blood compartment of the dialyzer. A prepared solution of dialysate is passed through the dialysate compartment of the dialyzer. The wastes from the blood pass through the medium by osmosis, ionic transfer or fluid transport into the dialysate and, depending upon the type of dialysis treatment, desirable components from the dialysate may pass in the opposite direction through the medium and into the blood. The transfer of the wastes from the blood into the dialysate cleanses the blood while allowing the desired components from the dialysate to enter the bloodstream.

The dialysate must be heated before it is passed through the dialyzer. Since the dialyzer functions as a heat exchanger, it is important that the dialysate be at approximately the patient's body temperature. The flow rate of dialysate is generally high enough that a substantial amount of electrical power is consumed by the heater to raise the temperature of the dialysate to body temperature. The required increase in temperature may be substantial since the major component of dialysate is water, and the entering water temperature may be relatively low, for example as low as 5 degrees C. If the heater does not supply an adequate amount of heat, the flow rate of the dialysate must be reduced to attain the desired temperature elevation. Reducing the flow rate of the dialysate may require a directly related reduction in the flow of blood, which may in turn extend the time required to complete the dialysis treatment.

Of course, the dialysis treatment can not begin until the dialysate temperature is raised to body temperature. The initial time required to heat the dialysate before the treatment begins is referred to as a warm-up time. The warm-up time normally starts after the patient is connected to the dialysis machine, and can seem relatively long to the patient.

Heaters are also used in dialysis machines to elevate the temperature of a cleaning solution during a cleaning and disinfecting procedure applied prior to using the dialysis machine. During the cleaning and disinfecting procedure, a chemical disinfectant is circulated through the flow path through which the dialysate normally flows during dialysis treatments. Heating the cleaning solution assists in killing microorganisms which might be transferred through the dialysis medium into the blood. It is typical that the temperature of the cleaning solution is relatively high, almost to the boiling point. A relatively significant amount of power is consumed to elevate the cleaning and disinfecting solution to a desirable temperature.

Heaters in dialysis machines are typically electric. In those geographic regions of the world where the typical commercial electrical service is supplied at 230 volts, an adequate amount of electrical power is generally available to heat the dialysate and the cleaning and disinfecting solution at an acceptable rate. However in those geographic areas where the commercial electrical service is supplied at 115 volts, the heating capacity of the heater is frequently limited enough to extend the length of the cleaning and disinfecting time, the warm-up period and even possibly the dialysis treatment time if the dialysate can not be heated at an adequate rate commensurate with the desired blood flow rate. While it is always possible to install a 230 volt electrical service, the cost of installation is frequently considered to be prohibitive.

Another contributing factor to the limited power delivery from heaters in dialysis machines is the safety regulations pertaining to dialysis machines. Generally, these regulations limit the amount of power that may be consumed by a dialysis machine to approximately 80% of the maximum power available from a typical single-circuit electrical service. Generally speaking, the typical single circuit electrical service is a 15 amp, 115 volt circuit. Consequently, of the approximately 1725 watts of available power, approximately only 1380 watts are available for use by the dialysis machine.

Not all of the power consumed by the dialysis machine is available for the heater. The other components of the dialysis machine require electrical power, such as the blood and dialysate pumps, cathode ray tube monitors, clamps and valves, and the system microcontrollers, among others. The amount of power available to the heater depends on how much power the other components use, because the function of these other components is essential to the performance of the dialysis treatment. From a priority standpoint, these other components, if in use during the treatment, must receive electrical power. Thus, since it is always possible to reduce the treatment flow rates without compromising the patient's safety, the available power to the heater has been limited to accommodate the other more critical components of the machine.

For example, the typical prior approach has been to predetermine the amount of power that each system of components within the machine will consume on a worst case basis. The worst case power consumptions are added, and the total is subtracted from the maximum allowed power consumption of the dialysis machine. The result is the amount of power available to the heater. The capacity of the heater is selected to provide that maximum amount of heat.

As a consequence of this approach to determining the capacity of the heater, the maximum amount of heat available for heating the dialysate is limited to the worst case consumption of all of the remaining components of the dialysis machine concerning their full allotted amounts of power. The practical reality is, however, that the other components very rarely if ever consume the maximum amount of power simultaneously. Nonetheless, because of the worst-case allocation approach to sizing the capacity of the heater, no additional power may be supplied for heating the dialysate.

It is with respect to these problems and other concerns and issues that the present invention has been developed.

SUMMARY OF THE INVENTION

An important aspect of this invention is to maximize the amount of electrical power available for use by the dialysate heater in a dialysis machine while still assuring that the other components of the dialysis machine will receive power as needed on a priority basis to maintain safe patient conditions during treatment. Another aspect of this invention is to reduce the amount of time required to clean and disinfect a dialysis machine prior to its use. A further aspect of the machine is to reduce the warm-up time period prior to dialysis treatment. Still another aspect of the invention is to maximize the amount of heating capacity from the heater without exceeding the maximum allowed power consumption of the dialysis machine. A further aspect of this invention is to achieve the foregoing aspects of this invention in a dialysis machine intended to be powered from 115 volt electrical service, and thereby avoid the costs changing the electrical service in dialysis clinics.

In accordance with these and other aspects, the present invention is generally directed to an improved dialysis machine and a method of regulating the amount of electrical power delivered to a dialysate heater of the dialysis machine without substantially exceeding a predetermined maximum allowed power consumption for the dialysis machine. The dialysis machine includes apparatus, which executes and the method generally involves, the functions of measuring an amount of instantaneous or actual power consumed by the machine, comparing the instantaneous power consumed to the maximum allowed power consumption to determine any excess of power beyond the instantaneous power consumed up to the maximum allowed power consumption, and making the excess power available for use by the heater. In this manner any excess power available over the maximum allowed power consumption of the machine will be available for use in heating dialysate. The instantaneous power consumed (relative to the maximum allowed power consumption) governs the heat available from the heater. The artificial limitations of worst case power consumption do not adversely affect the heat available from the heater, thereby increasing the rate at which dialysis treatments may progress and reducing the time required for dialysis treatments. Corresponding decreases in the costs of dialysis treatments may also occur if more treatments can be performed during a given time period.

A more complete appreciation of the present invention and its scope may be obtained from the accompanying drawings, which are briefly summarized below, from the following detailed descriptions of presently preferred embodiments of the invention, and from the appended claims.

DETAILED DESCRIPTION

Figure 1:
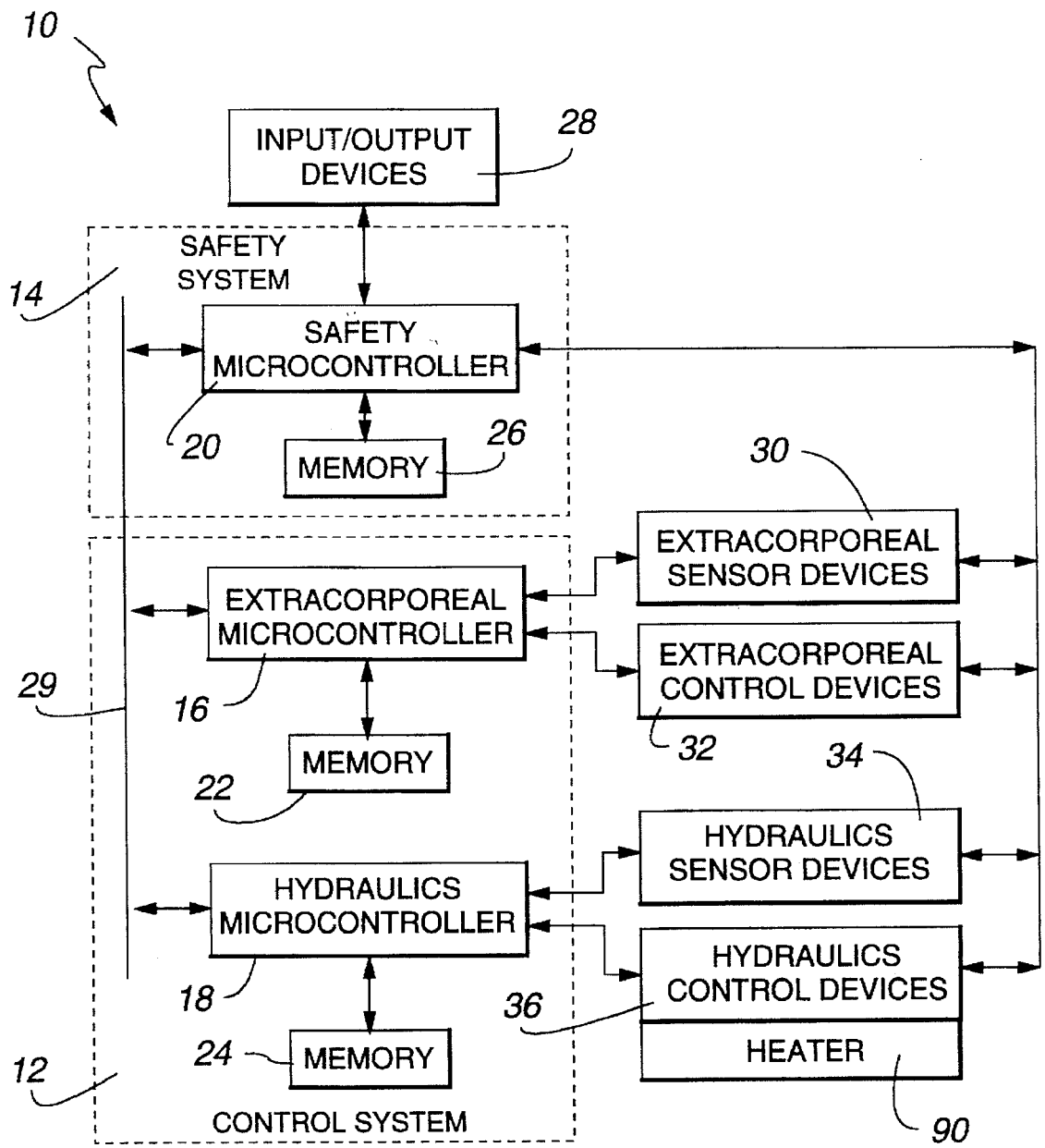
FIG. 1 is a block diagram of a control system and a safety system of a dialysis machine which incorporates the present invention.

The present invention is advantageously incorporated in a dialysis machine, such as that shown generally at 10 in FIG. 1. The dialysis machine 10 is used to perform a variety of different and well-known dialysis treatments on a patient. To perform the dialysis treatments adequately and to protect the patient from risks during the treatment, the dialysis machine 10 includes a control system 12 and a safety system 14. Control system functionality is typically accomplished by an extracorporeal microcontroller 16 and a hydraulics microcontroller 18. The safety system 14 includes a safety system microcontroller 20. Each microcontroller 16, 18 and 20 includes its own memory 22, 24 and 26 respectively, in which programs are recorded for controlling the microcontrollers and the components of the dialysis machine 10.

Control and safety information is supplied to the dialysis machine through an operator/machine interface (OMI). The OMI typically includes an input/output (I/O) device 28 through which the entered information is supplied to the safety microcontroller 20 and from which operating and safety information is displayed to the operator. Information is directly transferred and shared between the microcontrollers 16, 18 and 20 over a bus or network 29.

In addition, components of the dialysis machine 10 establish an extracorporeal flow path and a hydraulics flow path. Blood from the patient flows through the extracorporeal flow path where it is cleansed and then returned to the patient. Dialysate flows through the hydraulics flow path to remove the wastes transferred to the dialysate. The extracorporeal flow path includes sensors 30 and control devices 32 to sense blood flow conditions and control the blood flow. Similarly the hydraulics flow path also includes sensors 34 and control devices 36 to sense characteristics of the dialysate and control its flow rate and other characteristics such as temperature and conductivity.

The sensors and the control devices located in the extracorporeal and the hydraulics flow paths are connected to both the control system 12 and the safety system 14. This redundancy allows either system to assume control over the dialysis machine 10 and place it in a safe patient state should the need arise.

Figure 2:
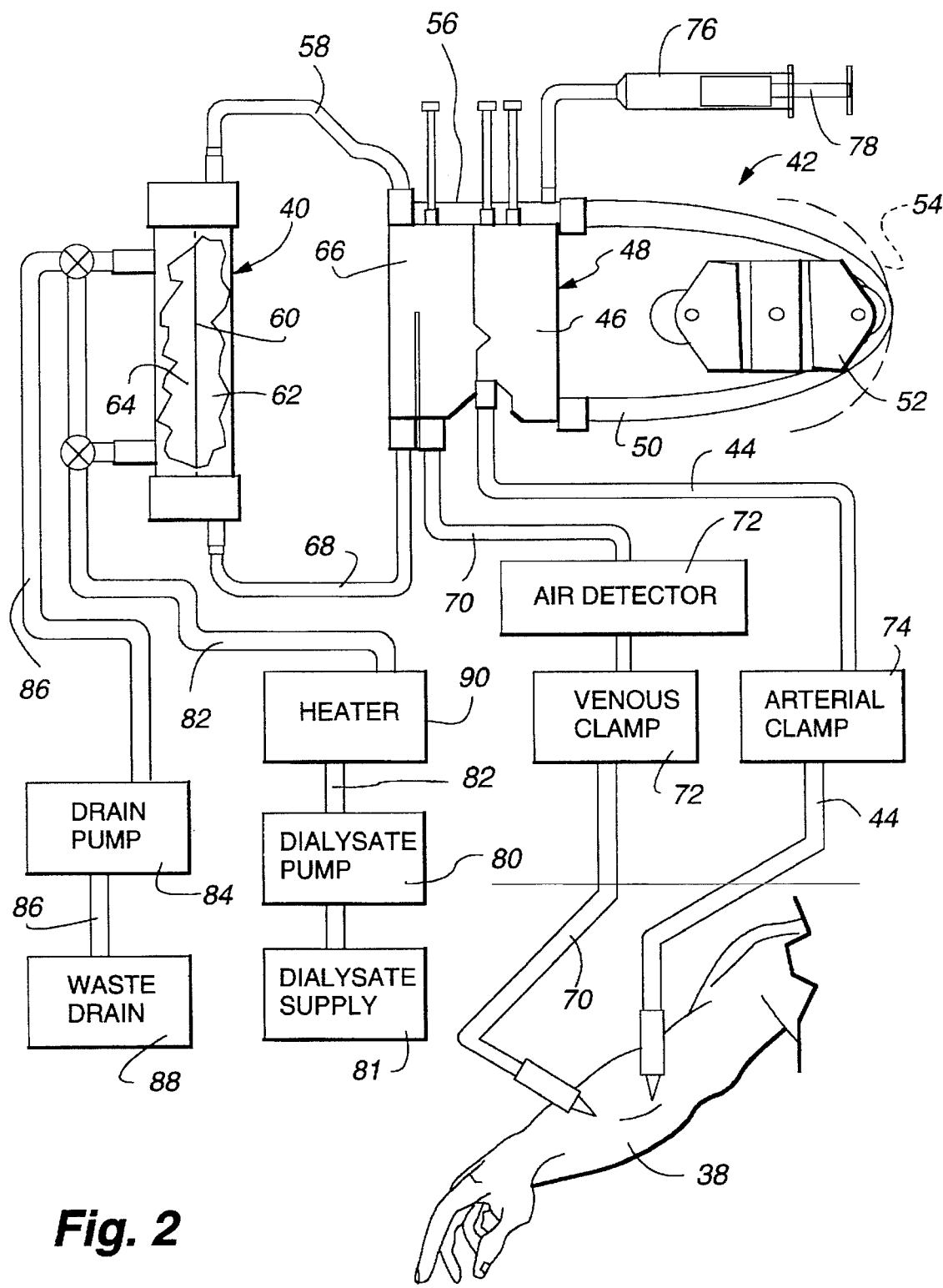
FIG. 2 is a generalized view illustrating some of the typical components of the dialysis machine shown in block diagram form in FIG. 1.

More details concerning the extracorporeal flow path are shown in FIG. 2. Blood flows from a patient 38, through a conventional dialyzer 40, and back to the patient 38. An arterial blood pump 42 (usually peristaltic, as shown) draws blood from the patient 38 through an arterial line 44 and into an arterial chamber 46 of a blood handling cartridge 48. The blood pump 42 pumps blood from the arterial chamber 46 through a pump tubing 50, around a rotating rotor 52, by a stationary raceway 54, through a manifold 56 and tube 58 and into the dialyzer 40.

A micro-porous or other type of dialysis medium 60 divides the interior of the dialyzer 40 into a blood chamber 62 and a dialysate chamber 64. The blood is cleansed in the dialyzer 40 in the usual manner and then transferred through a tube 68 to a venous chamber 66 where any air in the blood may be extracted.

After leaving the venous chamber 66 the blood flows through a venous line 70 to an air detector 72. If an excessive amount of air is present, a venous line clamp 74 will immediately close to terminate the flow of blood before the air reaches the patient 38. Similarly, an arterial clamp 75 is located in the arterial line 44 to stop the flow of blood when necessary or desired.

An anticoagulant is slowly delivered to the extracorporeal flow path from a syringe 76. A plunger 78 is displaced into the syringe 76 by a driver mechanism (not shown) which is controlled by the control system.

The elements of the hydraulics flow path are also shown in greater detail in FIG. 2. The hydraulics flow path includes a number of different valves (most of which are not shown) and a dialysate pump 80 which draws dialysate from a supply 81. The supply 81 is typically a mixture of chemicls and water which the dialysis machine prepares as the dilysate is used or a previously prepared quantity of dialysate. The dialysate pump 80 delivers the dialysate from the supply 81 through a dialysate supply line 82 to the dialysate chamber 64 of the dialyzer 40. The dialysate flows past the medium 60 where it absorbs the waste products transferred through the medium 60 from the blood in the blood chamber 62. Any beneficial components within the dialysate which are desired to be transferred to the blood pass through the medium 60 and into the blood in the blood chamber 62.

Dialysate containing the waste products is removed from the dialysate chamber 64 by a drain pump 84 which is connected to the dialyzer 40 by a dialysate drain line 86. The used dialysate in the dialysate drain line 86 is delivered to a waste drain 88.

Prior to entering the dialyzer 40, the dialysate is heated in a heater 90. The heater 90 is located in the dialysate supply line 82 and is typically of the flow-through type. As a flow-through heater, the dialysate must be elevated to the desired temperature as the dialysate flows through the heater. In other words, the heater 90 does not establish a reservoir of heated dialysate. Consequently the flow rate through the dialysate supply line 82 must be controlled in relation to the heat capacity of the heater 90 so that the dialysate leaving the heater 90 and entering the dialyzer 40 is at the proper temperature to avoid cooling or heating the blood excessively in the extracorporeal flow path as the blood flows through the dialyzer 40. Temperature sensors (not shown) are located in the dialysate supply line 82 to detect the temperature of the dialysate.

The control system 12 receives signals from the extracorporeal sensor devices 30 which are located in the extracorporeal flow path, as generally shown in FIG. 1. Based on the signals from the sensor devices 30 and the operating program located in the memory 22, the extracorporeal microcontroller 16 of the control system 12 controls the conventional flow-controlling devices which have generally been described in FIG. 2 and which are collectively shown at 32 in FIG. 1 to achieve the desired conditions within the extracorporeal flow path.

The hydraulics microcontroller 18 of the control system 12 receives signals from the hydraulics sensor devices 34 which are located in the hydraulics flow path, as is also generally shown in FIG. 1. Based on the signals from the sensor devices 34 and the operating program located in the memory 24, the hydraulics microcontroller 18 controls the conventional flow-controlling devices which have generally been described in FIG. 2 and which are collectively shown at 36 in FIG. 1 to achieve the desired conditions within the hydraulics flow path. The heater 90 is one of the control devices 36 located in hydraulics flow path which is specifically controlled by the hydraulics microcontroller 18 in accordance with the present invention.

The safety system of the dialysis machine 10 includes the safety microcontroller 20 which operates from a program recorded in the safety system memory 26. The safety system microcontroller 20 is connected to the extracorporeal sensor devices 30, the extracorporeal control devices 32, the hydraulics sensor devices 34 and the hydraulics control devices 36 separately of the connections of these elements to the control system microcontrollers. Thus, using the sensor signals in conjunction with the program recorded in its memory 26, the safey system 14 is capable of determining potentially risky conditions independently of the determination made by the control system 12. The safety system 14 also has the capability of assuming control over the extracorporeal and hydraulics flow paths due to the independent connection to the extracorporeal and hydraulics control devices 32 and 36 so that it can place the dialysis machine 10 in a safe patient state if necessary.

As is apparent from the description of the dialysis machine 10, all of its functionality is controlled and monitored through the use of electrical power consuming components. Based on the instantaneous consumption of electrical power by the remaining components of the dialysis machine, the present invention offers the capability of maximizing the electrical power available for use by the heater 90. In general, the basic aspects of the invention involve measuring the amount of power instantaneously consumed by the dialysis machine, comparing the power consumed to the maximum allowed power consumption of the dialysis machine, and making available to the heater any excess of power beyond that consumed up to the maximum allowed power consumption of the machine. Of course, additional power is delivered to the heater only if the control microcontrollers determine that additional heat from the heater would enhance the progress of the dialysis treatment.

Figure 3:
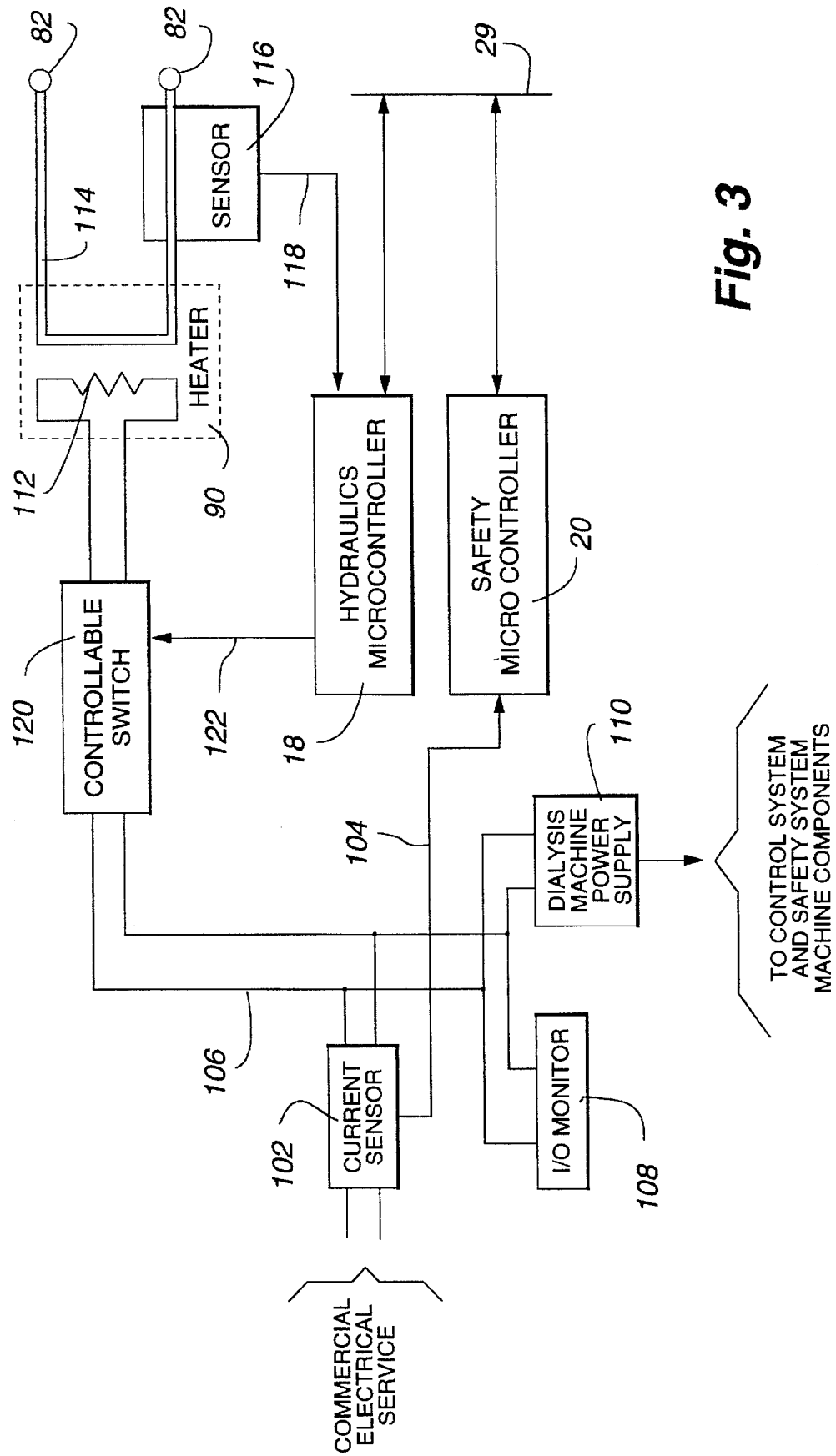
FIG. 3 is a more detailed block diagram of some of the components of the control system and safety system of the dialysis machine shown in FIG. 1.

The aspects of the invention which relate primarily to sensing the power consumed by the dialysis machine and controlling the power delivered to the heater are shown and described in conjunction with FIG. 3. The dialysis machine consumes power from a conventional commercial AC electrical service referenced generally at 100. The power consumed by the machine is passed through a current sensor 102. The current sensor develops a signal at 104 which relates to the magnitude of AC current delivered to the machine. Since the voltage from the electrical service 100 is constant and known, the current signal 104 is directly related to the power consumed by the machine. The current signal 104 is supplied to the safety microcontroller 20, where the safety microcontroller utilizes the current signal 104 to determine the instantaneous amount of power consumed by the dialysis machine.

The AC power is delivered to the machine over AC power main conductors 106. The AC conductors distribute the AC power within the dialysis machine for two basic uses. One use of the power is by the heater 90. The other use of the power from the AC conductors 106 is by the other electrical components of the dialysis machine. Those components include a cathode ray tube monitor 108 which directly operates from the applied AC current. The other category of electrical components within the dialysis machine typically operate from low voltage DC power delivered by a power supply 110. The components connected to the power supply 110 include all of those associated with the control system and safety system except the heater 90 and the monitor 108 and any other components which might operate directly from the applied AC power on the main conductors 106.

The heater 90 includes a resistive heating element 112 which converts the applied AC current from the main conductors 106 into heat. The heat from the heating element 112 is conducted to a conduit 114 of the heater 90. The conduit 114 is located in the dialysate supply line 82, and the dialysate which flows through the conduit 114 absorbs the heat generated by the resistive element 112.

A sensor 116 is connected to the conduit 114 to develop a temperature signal at 118. The temperature signal 118 is directly related to the temperature of the dialysate which flows out of the conduit 114 of the heater 90. The temperature signal 118 is supplied to the hydraulics microcontroller 18, where the hydraulics microcontroller uses the temperature signal 118 as the basis for controlling the amount of electrical current delivered to the resistive heating element 112.

A conventional controllable switch 120 controls the delivery of AC power from the main conductors 106 to the heating element 112. The controllable switch 120 is preferably an optically isolated relay which becomes conductive and nonconductive in response to control signals supplied at 122 from the hydraulics microcontroller 18. The hydraulics microcontrollers delivers the control signals 122 in response to information supplied by the safety microcontroller 20 over the network 29.

One effective manner of controlling the power delivered to the heater is by duty cycle regulation. A duty cycle is regularly repeating interval during which the switch 120 is on or conductive for a part of that interval and is off or nonconductive for the remaining part of that interval. Obviously, if the switch 120 is conductive more than it is nonconductive, more power will be transferred to the heating element 112. Conversely if the switch 120 is nonconductive more than it is conductive, less power will be transferred to the heating element 112.

The duty cycle is often expressed as a percentage. This percentage is the ratio of the conductive time to the total time interval. For example, during a one second time interval, if the switch is conductive for a half second, the duty cycle would be 50%. If the time interval is small enough, the temperature can be regulated very closely without limiting the ability of the heater to rapidly increase the heat output if desired.

Figure 4:
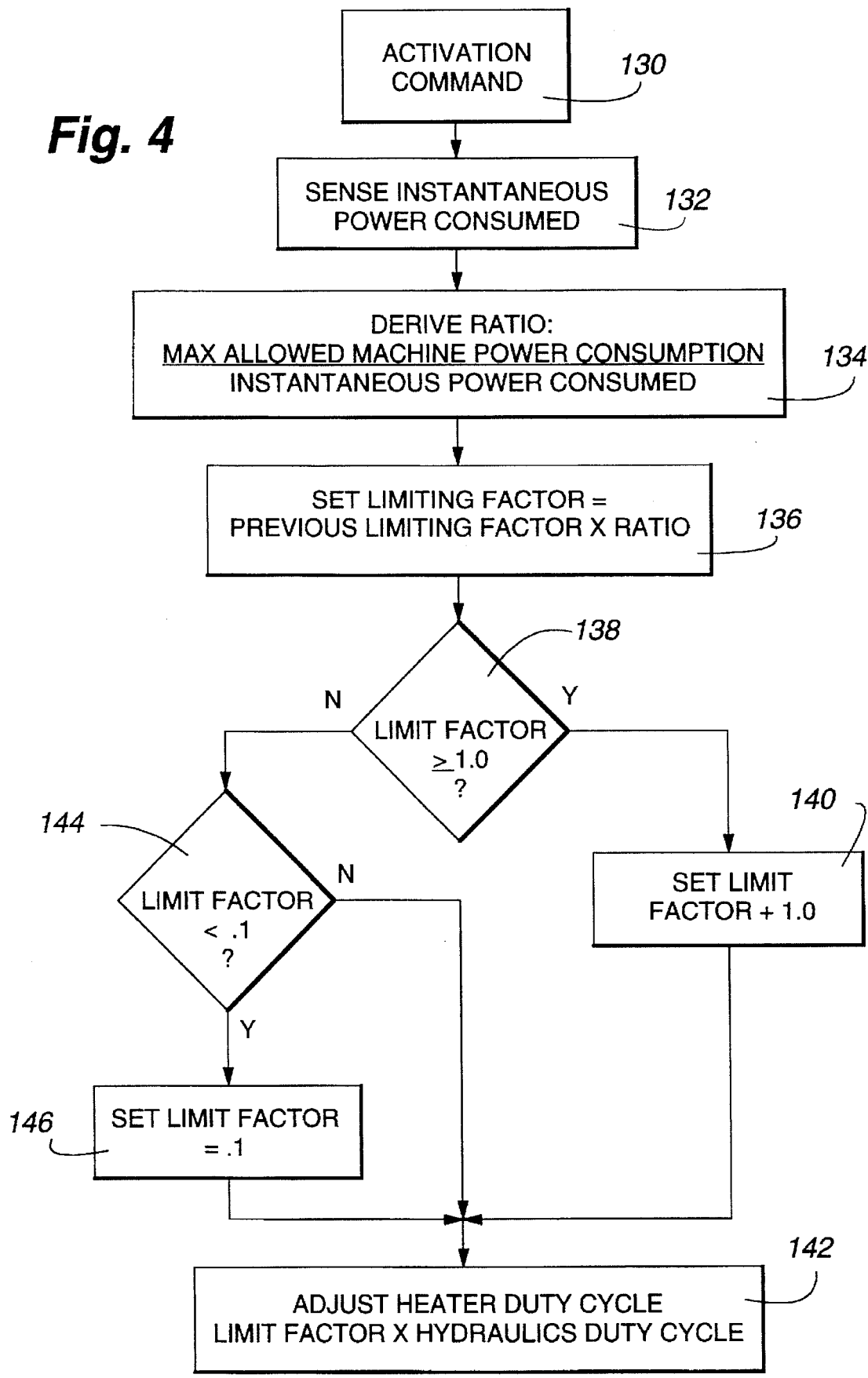
FIG. 4 is a flow chart of the functions performed by a control system microcontroller shown in FIG. 3 during execution of the present invention.

The manner in which the microcontrollers 20 and 18 cause the control signals 122 to deliver AC power to the resistive heating element 112 and thereby maximize the heat transfer to the dialysate in relation to the other power requirements of the dialysis machine is shown by the flow chart shown in FIG. 4. The steps shown in FIG. 4 are preferably executed by the microcontrollers 18 and 20. Each of the steps shown in the flow chart of FIG. 4 are separately designated by reference numbers for convenience of description.

In general, the starting point is to allow the hydraulics microcontroller 18 (FIG. 3) to deliver power to the heater 90, without regard to the maximum allowed power consumption of the dialysis machine, based on the desired amount of heat to be delivered to the dialysate as determined by the hydraulics microcontroller itself. Thus, in the initial instance, the hydraulics microcontroller establishes the duty cycle for energizing the heater. Thereafter, however, the safety microcontroller 20 (FIG. 3) calculates a limiting factor to determine whether the duty cycle established by the hydraulics microcontroller should be limited because that duty cycle results in the dialysis machine consuming an excess of power beyond the maximum allowed power consumption. If the power must be reduced, the limiting factor calculated by the safety microcontroller is delivered to the hydraulics microcontroller, and the hydraulics microcontroller adjusts the duty cycle by the limiting factor. Stated somewhat differently, the management system is allowed to establish initially the desired amount of power delivery according to its normal functionality, and thereafter the safety system limits the amount of desired power consumption by the heater in a degree which results in the maximum power consumption of the dialysis machine while not substantially exceeding that established value. It should be noted that the control system could also perform similar functionality in executing this invention as that functionality is discussed for the safety microcontroller.

Execution of the functionality of limiting the power consumption of the heater as otherwise established only when necessary to avoid exceeding the maximum allowed power consumption of the dialysis machine is shown in FIG. 4. The program flow begins with an activation command shown at 130. The activation command is delivered by the hydraulics microcontroller to the safety microcontroller whenever the hydraulics microcontroller determines that a change of the duty cycle previously established is necessary. Alternatively, the activation command could be generated on a regular periodic basis by the safety microcontroller to maintain a recurring evaluation of the power consumption of the dialysis machine.

The next step at 132 involves sensing the instantaneous power consumed by the dialysis machine. This step 132 is accomplished by the safety microcontroller 20 (FIG. 3) reading the current signal 104 delivered by the current sensor 102. As previously explained, the current signal 104 is directly related to the instantaneous power consumed by the dialysis machine. Any relative phase angle between the delivered voltage and the delivered current may be ignored if the dialysis machine exhibits a primarily resistive characteristic, or simply for convenience of calculation since the power consumption will never exceed a unity phase angle between the applied voltage and current which is assumed in the direct relationship used in this example.

The memory 26 (FIG. 1) of the safety microcontroller 20 has information recorded in it which describes the maximum allowed power consumption of the dialysis machine. As discussed previously the maximum allowed power consumption is generally 80% of the typical electrical service capacity of a standard individual circuit. The maximum allowed power consumption will generally be determined by the manufacturer of the dialysis machine at the time the machine is manufactured. The manufacturer will usually allow for some margin of error in determining this value, therefore if some overshoot occurs the machine will not violate governmental regulations. Even though the manufacturer will usually set the maximum allowed power consumption, it might conceivably be a variable or parameter which the user could establish. The concurrently filed application for "GRAPHICAL OPERATOR MACHINE INTERFACE AND METHOD FOR INFORMATION ENTRY SELECTION FOR A DIALYSIS MACHINE", Ser. No. 08/483,456, filed concurrently herewith describes a technique of programming various variables into a dialysis machine to control its functionality in a manner particularly suited to the individual user. Such a programing technique could be employed by the user to establish the maximum allowed power consumption as a parameter of operation.

A ratio of the maximum allowed power consumption to the instantaneous power consumed is next derived at 134. The ratio derived at 134 represents a value which indicates whether the power to the heater could be increased or should be decreased. A ratio greater than 1 indicates that additional power could be delivered to the heater 90 without exceeding the maximum allowed power consumption of the dialysis machine. A ratio less than 1 indicates that the power consumption of the dialysis machine has already exceeded the maximum allowed power consumption.

A limiting factor is thereafter derived at 136 using the ratio determined at 134. THE limiting factor is supplied by the safety microcontroller 20 (FIG. 3) to the hydraulics microcontroller 18 over the network 29. The limiting factor is used by the hydraulics microcontroller to limit the duty cycle which it has previously established to control the heat delivery from the heater 90. In general terms, the limiting factor is effective only to reduce the amount of current delivered to the heater. If the instantaneous consumed power is less than the maximum allowed power consumption, the limiting factor will not play a role in the duty cycle established by the hydraulics microcontroller. The hydraulics microcontroller will establish the amount of current desired to be delivered to the heater, and the limiting factor will play a role only when the instantaneous consumed power exceeds the maximum allowed power consumption of the machine.

The limiting factor set at 136 is the ratio established at 134 multiplied by the previously established limiting factor which was established in the immediately preceding iteration through the program flow shown in FIG. 4. A residual effect from the previous limiting factor is therefore retained in establishing the new limiting factor. This residual effect avoids rapid changes in the limiting factor and thereby assists in more precise regulation without oscillatory effects. Since the program flow shown in FIG. 4 may reoccur as often as the hydraulics microcontroller determines a need for the change in heat delivered, or on a regular periodic basis, the residual effect of the previous limiting factor does not significantly reduce performance.

The limiting factor established at 136 is compared to a unity value at 138. If the comparison reveals that the limiting factor is greater than unity, there is excess power available that may be delivered to the heater. If the limiting factor is greater than unity, the limiting factor is set to unity at 140. Setting the limiting factor to unity simply allows the hydraulics microcontroller to control the power delivery to the heater without a limiting effect.

The step 142 illustrates that the unity power factor has no effect on the duty cycle established by the hydraulics microcontroller. The unity power factor does not increase or decrease the duty cycle established by the hydraulics microcontroller.

If the comparison at 138 reveals that the limiting factor is less than 0.1, as determined at 144, the limiting factor is set at a fixed minimum value of 0.1 at 146. Setting the limiting factor to the fixed minimum value of 0.1 establishes the maximum rate of decrease in the duty cycle set at 142. Adjusting the duty cycle at 142 by multiplying the previous duty cycle by the limiting factor established at 146 causes a substantial reduction in power consumed by the heater. Limiting the maximum reduction in the duty cycle also enhances the regulation capability without reducing adverse control effects, but still obtains relatively rapid decreases in power consumed by the heater if necessary.

If the limiting factor set at 136 is between the values of 0.1 and 1.0, which is determined by the comparisons at 138 and 144, the limiting factor is directly used to adjust the duty cycle established by the hydraulics microcontroller, as shown at 142. Multiplying the duty cycle by the limiting factor between the values of 0.1 and 1.0 causes the power consumed by the dialysis machine to remain at essentially the maximum allowed power consumption.

After accomplishing any adjustment required by the program flow illustrated in FIG. 4, the process will be repeated upon the next iteration when the activation command 130 is delivered. It should also be noted that each iteration which results in a change in the power consumed by the heater is also likely to change the power consumed by the dialysis machine. Such changes in power consumption will be sensed by the sensor 102 (FIG. 3) and those changes will be reflected in the instantaneous power consumed sensed at 132.

By using the current sensor and the duty cycle adjustment features, the present invention is effective to maximize power to the heater when desired, provided that an increase in power is desired and additional power is available without exceeding the maximum allowed power consumption for the dialysis machine. As a result, the time of dialysis treatments or the rate of treatment is not artificially limited by arbitrary fixed allocations of power to the different Systems and components of the dialysis machine. The amount of time required to clean and disinfect a dialysis machine prior to its use is reduced. The warm-up period before the treatment starts can also be reduced. Power regulation effects are achieved in connection with the maximized power delivery potential to avoid or substantially reduce the oscillatory effects of feedback control. The safety microcontroller exercises the typical safety functions in the manner intended, and the hydraulics microcontroller responds to the pre-emptive safety control intended for the dialysis machine.

A presently preferred embodiment of the present invention and many of its improvements have been described with a degree of particularity. This description is a preferred example of implementing the invention, and is not necessarily intended to limit the scope of the invention. The scope of the invention is defined by the following claims.

The invention claimed is:

1. A dialysis machine which consumes electrical power supplied from an electrical service but which is limited by a predetermined maximum allowed electrical power consumption value, the dialysis machine including an electrical heater for heating dialysate supplied to a dialyzer to a selected temperature during a dialysis treatment, the dialysis machine also including components other than the heater, the heater and the other components consuming electrical power supplied to the machine from the electrical service, the dialysis machine also including a power management system operative to regulate the relative amount of electrical power delivered to the heater and to the other components without exceeding the predetermined maximum allowed electrical power consumption value, the power management system comprising:

a power sensor connected to the electrical service and operative to supply a power signal related to an amount of instantaneous power consumed by the machine; and a controller responsive to the power signal and operative to:

derive a power consumed value from the power signal, the power consumed value related to the power actually consumed by the dialysis machine;

compare the power consumed value to the predetermined maximum allowed electrical power consumption value; and in response to the comparison control the total amount of power delivered to the heater to make available the maximum amount of power to the heater which still assures supply of power needed for consumption by the other components while simultaneously regulating the total power consumption of the dialysis machine to a value not substantially exceeding the predetermined maximum allowed electrical power consumption value.

2. A dialysis machine as defined in claim 1 further including a temperature regulator connected to the heater and responsive to dialysate temperature during the treatment to regulate an amount of power delivered to the heater, and wherein the controller is further operative to:

limit the amount of power which the temperature regulator can cause to be delivered to the heater.

3. A dialysis machine as defined in claim 2 wherein the controller is further operative to:

reduce the amount of power which the temperature regulator can cause to be delivered to the heater by an amount proportional to a ratio of the predetermined maximum allowed electrical power consumption value to the power consumed value.

4. A dialysis machine as defined in claim 3 wherein the controller is further operative to:

reduce the total amount of power delivered to the heater only when the temperature regulator attempts to deliver power to the heater in an amount which would result in an increase in the power consumed to a value greater than the predetermined maximum allowed electrical power consumption value.

5. A dialysis machine as defined in claim 2 wherein the controller is further operative to:

limit the total amount of power delivered to the heater only when an increase in the total amount of power delivered to the heater would result in the instantaneous power consumed value increasing above the predetermined maximum allowed electrical power consumption value.

6. A dialysis machine as defined in claim 2 further including a control system functionality for controlling the operation of the dialysis machine during normal treatment and a safety system functionality for monitoring the proper operation of the machine during the normal treatment and for assuming control over the machine under an abnormal safety condition, wherein the temperature regulator is a part of the control system functionality, and wherein:

the power sensor and the controller are incorporated in the safety system functionality; and the safety system functionality controls the control system functionality to limit the total power delivered to the heater.

7. A dialysis machine as defined in claim 6 wherein the temperature regulator is incorporated in the control system functionality.

8. A dialysis machine as defined in claim 7 wherein the temperature regulator delivers power to the heater on a duty cycle basis, and wherein the controller is further operative to:

supply a control signal to the temperature regulator by which to adjust an on time of the duty cycle of power delivered to the heater.

9. A dialysis machine as defined in claim 2 wherein the temperature regulator delivers power to the heater on a duty cycle basis, and wherein the controller is further operative to:

reduce an on time of the duty cycle by an amount proportional to a ratio of the predetermined maximum allowed electrical power consumption value to the power consumed value.

10. A method of regulating electrical power delivered to a dialysate heater to heat dialysate in a dialysis machine without substantially exceeding a predetermined maximum allowed power consumption of the dialysis machine, comprising the steps of:

measuring instantaneous power consumed by the machine;

comparing the instantaneous power consumed by the machine to the maximum allowed power consumption;

determining from the comparing step any excess of power beyond the instantaneous power consumed up to the maximum allowed power consumption;

making the excess power available for use by the heater.

11. A method as defined in claim 10 further comprising the steps of:

regulating the power delivered to the heater to maintain a desired dialysate temperature; and using the excess power only to the extent made available to regulate the desired temperature of the dialysate.

12. A method as defined in claim 11 further comprising the steps of:

regulating the power delivered to the heater by applying power on a duty cycle basis to the heater;

delivering power to the heater during an on time of each duty cycle and terminating the power delivery to the heater during an off time of each duty cycle; and adjusting the on time of each duty cycle to regulate the power delivered to the heater to a value which does not result in total power consumption of the dialysis machine substantially exceeding the predetermined maximum allowed power consumption.

13. A method as defined in claim 12 further comprising the steps of:

limiting the adjustment the on time of each duty cycle by an amount equal to a ratio of the predetermined maximum allowed power consumption to the instantaneous power consumed.

14. A method of regulating electrical power delivered to a dialysate heater to heat dialysate in a dialysis machine without substantially exceeding a predetermined maximum allowed power consumption of the dialysis machine, comprising the steps of:

establishing a desired amount of power to be delivered to the heater according to a desired temperature of the dialysate and without regard to power consumed by the dialysis machine;

sensing an instantaneous power consumed by the dialysis machine;

determining whether the instantaneous power consumed is greater than or less than the predetermined maximum allowed power consumption;

reducing the desired amount of power to be delivered to the heater if the instantaneous power consumed is greater than the predetermined maximum allowed power consumption; and delivering the desired amount of power to the heater if the instantaneous power consumed is less than the predetermined maximum allowed power consumption.

15. A method as defined in claim 14 further comprising the steps of:

calculating a ratio of the predetermined maximum allowed power consumption to the instantaneous power consumed; and reducing the desired amount of power to be delivered to the heater by multiplying the ratio and the desired amount of power established.

16. A method as defined in claim 15 further comprising the steps of:

bounding upper and lower values of the ratio to one and a predetermined value less than one which is selected to achieve regulatory control without significant oscillatory effects.

* * * * *